United States Patent
Lee et al.

(10) Patent No.: US 9,127,141 B2
(45) Date of Patent: Sep. 8, 2015

(54) METHOD OF PREPARING ESTER PLASTICIZER AND ESTER PLASTICIZER PREPARED THEREFROM

(71) Applicant: LG CHEM, LTD., Seoul (KR)

(72) Inventors: Mi Yeon Lee, Daejeon (KR); Hyun Kyu Kim, Daejeon (KR); Da Won Jung, Daejeon (KR); Dong Hyun Ko, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/340,881

(22) Filed: Jul. 25, 2014

(65) Prior Publication Data

US 2014/0336320 A1  Nov. 13, 2014

Related U.S. Application Data

(63) Continuation of application No. PCT/KR2014/004084, filed on May 8, 2014.

(30) Foreign Application Priority Data

| May 8, 2013 | (KR) | 10-2013-0051617 |
| Jun. 14, 2013 | (KR) | 10-2013-0068197 |
| Jun. 14, 2013 | (KR) | 10-2013-0068278 |

(51) Int. Cl.
  *C07C 67/293*  (2006.01)
  *C08K 5/12*  (2006.01)
  *C07C 67/03*  (2006.01)

(52) U.S. Cl.
  CPC .. *C08K 5/12* (2013.01); *C07C 67/03* (2013.01)

(58) Field of Classification Search
  CPC .................................. C08K 5/12; C07C 67/03
  USPC ........................................................... 562/480
  See application file for complete search history.

(56) References Cited

U.S. PATENT DOCUMENTS

| 5,101,064 A | 3/1992 | Dupont et al. |
| 7,361,779 B1 | 4/2008 | Holt et al. |
| 2007/0038001 A1 | 2/2007 | Cook et al. |
| 2007/0179229 A1 | 8/2007 | Grass |
| 2010/0305255 A1 | 12/2010 | Grass |

FOREIGN PATENT DOCUMENTS

| CN | 100999590 A | 7/2007 | |
| CN | 101657410 A | 2/2010 | |
| CN | 101679708 A | 3/2010 | |
| CN | 101823966 * | 9/2010 | ............. C07C 69/75 |
| CN | 101925571 A | 12/2010 | |
| EP | 1564234 A1 | 8/2005 | |
| FR | 2477535 A1 | 9/1981 | |
| JP | 2000-256274 | 9/2000 | |

(Continued)

*Primary Examiner* — John Uselding
(74) *Attorney, Agent, or Firm* — Dentons US LLP

(57) ABSTRACT

Provided is a method of preparing an ester plasticizer, more particularly, a method of preparing an ester plasticizer including conducting a transesterification reaction of a compound of Chemical Formula 1 with a first alcohol of Chemical Formula 2.
According to the preparation method according to an embodiment of the present invention, an ester plasticizer having high purity, yield, and process efficiency as well as excellent plasticizer properties such as processability and absorption rate may be easily prepared even under no catalyst.

22 Claims, 2 Drawing Sheets

(56) References Cited

FOREIGN PATENT DOCUMENTS

| JP | 2009-504645 A | 2/2009 |
| KR | 10-2007-0075341 | 7/2007 |
| KR | 10-2010-0116176 | 10/2010 |
| KR | 10-2013-0035493 A | 4/2013 |

* cited by examiner

METHOD OF PREPARING ESTER PLASTICIZER AND ESTER PLASTICIZER PREPARED THEREFROM

This application is a Continuation Bypass of International Application PCT/KR2014/004084, with an international filing date of May 8, 2014, which claims priority to and the benefit of Korean Patent Application No. 10-2013-0051617, filed May 8, 2013, Korean Patent Application No. 10-2013-0068197, filed Jun. 14, 2013, and Korean Patent Application No. 10-2013-0068278, filed Jun. 14, 2013, the disclosures of which are incorporated herein by reference in their entirety.

TECHNICAL FIELD

The present invention relates to a novel method of preparing an ester plasticizer and an ester plasticizer prepared therefrom.

BACKGROUND ART

Ester plasticizers are generally prepared by an esterification reaction between an acid and an alcohol. In this case, the esterification reaction is generally conducted under an acid catalyst or metal catalyst.

Currently, di-2-ethylhexyl phthalate is widely used as an ester plasticizer. However, the compound is an environmental hormone disturbing an endocrine organ and is harmful to human body. Also, there may be limitations in improving the processability and foamability of a resin.

Thus, there is a need to develop an environmentally-friendly ester plasticizer that may sufficiently improve the processability and foamability of the resin, and a preparation method that may effectively prepare the ester plasticizer.

DISCLOSURE OF THE INVENTION

Technical Problem

The present invention provides a novel method of preparing an ester plasticizer and an ester plasticizer having excellent plasticizer properties prepared therefrom.

The above and other objective of the present invention can be achieved by embodiments of the present invention described below.

Technical Solution

According to an aspect of the present invention, there is provided a method of preparing an ester plasticizer including conducting a transesterification reaction of a compound of Chemical Formula 1 with a first alcohol of Chemical Formula 2:

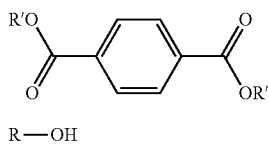   [Chemical Formula 1]

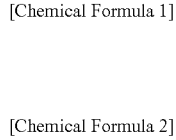   [Chemical Formula 2]

where R' is a non-branched $C_6$-$C_{12}$ alkyl or $C_6$-$C_{12}$ alkyl including at least one branched chain, R is a non-branched $C_4$-$C_{12}$ alkyl or $C_4$-$C_{12}$ alkyl including at least one branched chain, and R and R' are not the same as each other.

According to another aspect of the present invention, there is provided an ester plasticizer prepared by the preparation method.

According to another aspect of the present invention, there is provided a resin composition including the ester plasticizer and a thermoplastic resin.

Advantageous Effects

According to an embodiment of the present invention, an ester plasticizer having high purity, yield, and process efficiency as well as excellent plasticizer properties such as processability and absorption rate may be prepared even under no catalyst according to the novel method of preparing an ester plasticizer.

Also, since the transesterification reaction may not cause wastewater problems in comparison to an esterification reaction between acid and alcohol and may be performed under no catalyst conditions, limitations when using an acid catalyst may be addressed.

MODE FOR CARRYING OUT THE INVENTION

Figure 1:
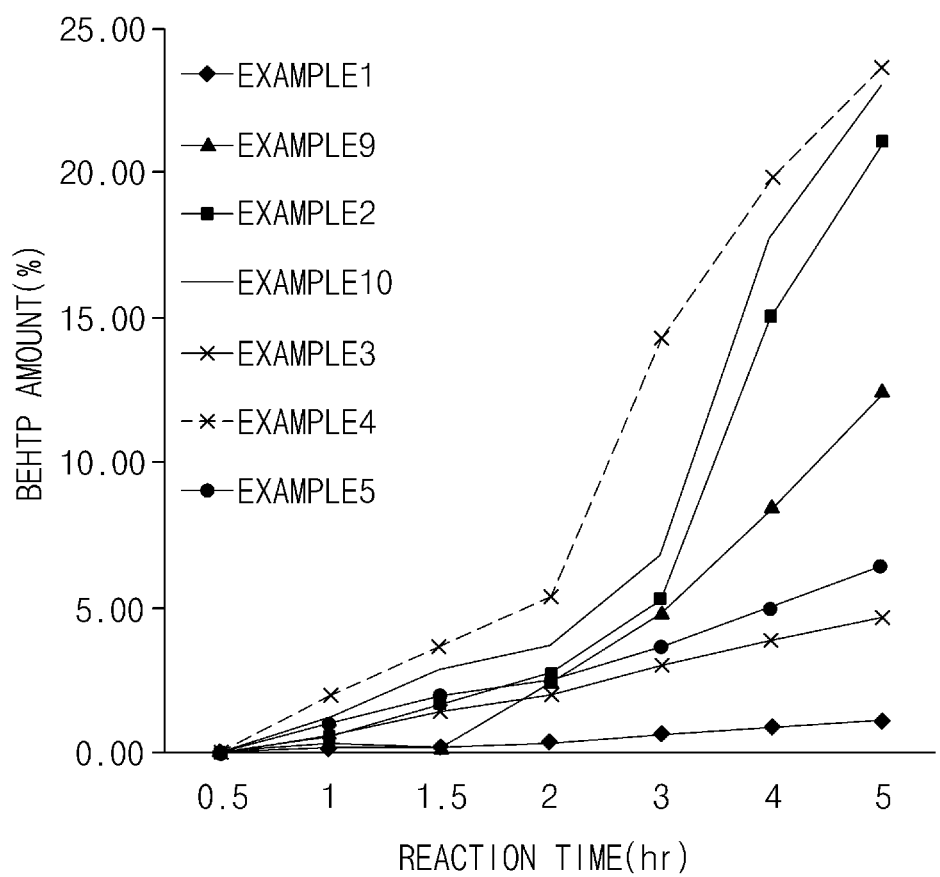
FIG. 1 is a graph illustrating changes in production amount (amount) of 1-butyl 4-(2-ethylhexyl)terephthalate (BEHTP) according to the adjustment of a reaction temperature of a transesterification reaction and the presence of a catalyst according to an embodiment of the present invention.

Hereinafter, the present invention will be described in detail.

A method of preparing an ester plasticizer of the present invention may include conducting a transesterification reaction of a compound of Chemical Formula 1 with a first alcohol of Chemical Formula 2:

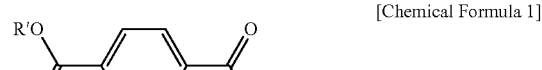   [Chemical Formula 1]

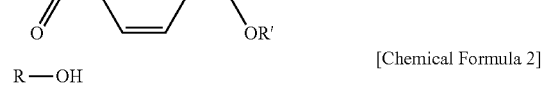   [Chemical Formula 2]

where R' is a non-branched $C_6$-$C_{12}$ alkyl or $C_6$-$C_{12}$ alkyl including at least one branched chain, R is a non-branched $C_4$-$C_{12}$ alkyl or $C_4$-$C_{12}$ alkyl including at least one branched chain, and R and R' are not the same as each other.

In the present invention, the ester plasticizer may denote ester compounds that are used or may be used as a plasticizer, a composition consisting of these compounds, or a composition comprising these compounds.

According to an embodiment of the present invention, an ester plasticizer having high purity, yield, and process efficiency as well as excellent plasticizer properties such as processability and absorption rate may be prepared even under no catalyst according to the novel method of preparing an ester plasticizer.

Also, since the transesterification reaction may not cause wastewater problems in comparison to an esterification reaction between acid and alcohol and may be performed under no catalyst conditions, limitations when using an acid catalyst may be resolved.

According to an embodiment of the present invention, the transesterification reaction may transform a portion of the compound of Chemical Formula 1 into a compound of the following Chemical Formula 5 and a compound of the following Chemical Formula 6:

[Chemical Formula 5]

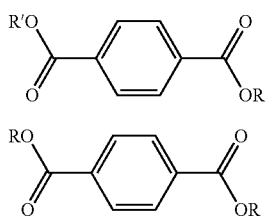

[Chemical Formula 6]

where R' is a non-branched $C_6$-$C_{12}$ alkyl or $C_6$-$C_{12}$ alkyl including at least one branched chain, R is a non-branched $C_4$-$C_{12}$ alkyl or $C_4$-$C_{12}$ alkyl including at least one branched chain, and R and R' are not the same as each other.

According to an embodiment of the present invention, by the transesterification reaction, the compound of Chemical Formula 1, the compound of Chemical Formula 5, and the compound of Chemical Formula 6 may be respectively formed in an amount of 25 wt % to 99 wt %, 0.5 wt % to 70 wt %, and 0.1 wt % to 20 wt % based on a total weight of the ester plasticizer, and preferably, may be respectively formed in an amount of 39 wt % to 85 wt %, 10 wt % to 60 wt %, and 0.5 wt % to 16 wt %. Furthermore, more preferably, the compound of Chemical Formula 1, the compound of Chemical Formula 5, and the compound of Chemical Formula 6 may be respectively formed in an amount of 46.7 wt % to 85 wt %, 14.5 wt % to 43.8 wt %, and 0.5 wt % to 9.5 wt %, and most preferably, may be respectively formed in an amount of 49.5 wt % to 83.2 wt %, 15.8 wt % to 42 wt %, and 1 wt % to 8.5 wt %.

An ester plasticizer having high process efficiency, excellent processability, and excellent absorption rate may be obtained within the above ranges.

The method of preparing an ester plasticizer according to an embodiment of the present invention will be described in detail below.

The compound of Chemical Formula 1 may be obtained by an esterification reaction between a compound of the following Chemical Formula 3 and a second alcohol of the following Chemical Formula 4 in the presence of a catalyst:

[Chemical Formula 3]

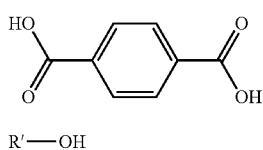

[Chemical Formula 4]

R'—OH where R' is a non-branched $C_6$-$C_{12}$ alkyl or $C_6$-$C_{12}$ alkyl including at least one branched chain.

The esterification reaction may be conducted in a temperature range of 80° C. to 270° C., and for example, may be conducted in a temperature range of 150° C. to 250° C. for 10 minutes to 10 hours, preferably, 30 minutes to 8 hours, and more preferably, 1 hour to 6 hours. In the above-described temperature range and reaction time range, the compound of Chemical Formula 1 may be effectively obtained.

According to an embodiment of the present invention, the catalyst may be an organic metal catalyst including a tin (Sn)-based or titanium (Ti)-based catalyst, an acid catalyst including a sulfonic acid-based or sulfuric acid-based catalyst, or a mixed catalyst thereof. However, the present invention is not limited to a kind of the catalyst.

According to an embodiment of the present invention, the compound of Chemical Formula 3 and the second alcohol of Chemical Formula 4 may be used in a molar ratio of 1:1 to 1:7, and preferably in a molar ratio of 1:2 to 1:5.

The compound of Chemical Formula 1 may be prepared in a yield of about 80% or more by the esterification reaction, and an ester plasticizer having a desired composition may be easily prepared by a transesterification reaction between the compound of Chemical Formula 1 thus prepared and the first alcohol of Chemical Formula 2.

The "transesterification reaction" used in the present invention denotes a reaction between the compound of Chemical Formula 1 prepared by the esterification reaction and the first alcohol of Chemical Formula 2 to interchange R' of the ester in the compound of Chemical Formula 1 with R in the alcohol, as illustrated in the following Reaction Equation 1.

[Reaction Equation 1]

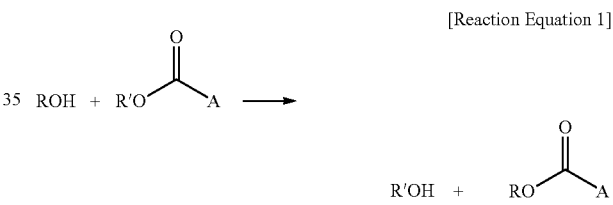

According to the transesterification reaction of the preparation method according to the embodiment of the present invention, the compound of Chemical Formula 6 may be formed when alkoxide of the alcohol of Chemical Formula 2 attacks carbon atoms in two ester groups (ACOOR') substituted at a phenyl group of Chemical Formula 1, and the compound of Chemical Formula 5 may be formed when the alkoxide of the alcohol of Chemical Formula 2 attacks the carbon atom in one ester group (ACOOR') substituted at the phenyl group of Chemical Formula 1; and the compound of Chemical Formula 1 may remain as an unreacted portion.

According to an embodiment of the present invention, the first alcohol of Chemical Formula 2, for example, may be added in an amount of 0.1 parts by weight to 89.9 parts by weight, preferably, 3 parts by weight to 50 parts by weight, more preferably, 4 parts by weight to 30 parts by weight, and most preferably, 4 parts by weight to 23 parts by weight based on 100 parts by weight of the compound of Chemical Formula 1. An ester plasticizer having high process efficiency and excellent improving effects of processability and foamability may be obtained within the above range.

A molar ratio of the compound of Chemical Formula 1 to the first alcohol of Chemical Formula 2, for example, is in a range of 1:0.005 to 1:5, 1:0.2 to 1:2.5, or 1:0.3 to 1:0.8. An ester plasticizer having high process efficiency and excellent improving effects of processability and foamability may be obtained within the above-described range.

For example, the transesterification reaction is conducted in a temperature range of 120° C. to 190° C., 135° C. to 180° C., 141° C. to 179° C., or 141° C. to 170° C., and an ester plasticizer having a desired composition may be obtained in a short period of time within the above range.

A reaction time of the transesterification reaction, for example, may be in a range of 0.1 hours to 10 hours, 0.5 hours to 8 hours, or 1 hour to 6 hours, and an ester plasticizer having a desired composition may be obtained economically within the above range.

In the preparation method according to the embodiment of the present invention, the reaction time may be calculated from the reaching point of a reaction temperature after increasing the temperature of reactants.

The transesterification reaction, for example, may be conducted under an acid catalyst or a metal catalyst. In this case, the reaction time may be decreased.

The acid catalyst, for example, may be sulfuric acid, methanesulfonic acid or p-toluenesulfonic acid, and the metal catalyst, for example, may be an organic metal catalyst, a metal oxide catalyst, a metal salt catalyst or a metal itself.

The metal, for example, may be any one selected from the group consisting of tin, titanium, and zirconium, or a mixture of one or more thereof.

According to an embodiment of the present invention, it may be more desirable to use the metal catalyst than the acid catalyst in terms of the control of by-products.

Also, the transesterification reaction, for example, may be a non-catalytic reaction. For example, the transesterification reaction may be efficiently conducted in a temperature range of 120° C. to less than 170° C. under no catalyst conditions.

In general, in a case where an ester plasticizer is prepared and a reaction which is not a transesterification reaction, for example, an esterification reaction is conducted, the reaction may be mostly performed under an acid catalyst for efficiently conducting the reaction. However, a large number of by-products may occur when the acid catalyst is used, and this may not only adversely affect physical properties of the resin composition, but may also be undesirable from an environmental aspect.

However, since the preparation method according to the embodiment of the present invention, i.e., the transesterification reaction may be performed even at a temperature of less than 170° C. under no catalyst conditions, limitations that may occur during the use of the catalyst and in a reaction above an activation temperature of the catalyst and in particular, limitations during the use of an acid catalyst may be addressed.

Thus, in the transesterification reaction according to an embodiment of the present invention, a boiling point of the first alcohol of Chemical Formula 2 may be a lower temperature than the activation temperature of the catalyst, and for example, the first alcohol of Chemical Formula 2 may have a boiling point of less than about 170° C.

In addition, since the transesterification reaction may be conducted under no catalyst, the transesterification reaction may not cause wastewater problems in comparison to an esterification reaction between acid and alcohol.

The method of preparing an ester plasticizer according to the embodiment of the present invention, for example, may further include removing unreacted first alcohol of Chemical Formula 2 after the transesterification reaction and alcohol formed as a reaction by-product by distillation.

For example, the distillation may be a two-stage distillation for separating the unreacted alcohol and the alcohol formed as a by-product by using a difference of boiling points.

As another example, the distillation may be a mixture distillation, and in this case, since changes in the composition of the plasticizer are small, a desired composition of the ester plasticizer may be relatively stably secured.

The mixture distillation of the present description denotes that the unreacted alcohol and the alcohol formed as a by-product are distilled at the same time.

According to an embodiment of the present invention, the first alcohol of Chemical Formula 2, for example, may be an alkyl alcohol having 4 to 12 or 4 to 10 carbon atoms, and excellent absorption rate and miscibility may be obtained within the above range.

According to an embodiment of the present invention, in Chemical Formulae 1 to 4, for example, a carbon number of R' may be greater than a carbon number of R.

Also, according to an embodiment of the present invention, in a case where R' of Chemical Formula 1 has at least one branched chain, R of Chemical Formula 2 is non-branched, and in a case where R' of Chemical Formula 1 is non-branched, R of Chemical Formula 2 may have at least one branched chain.

Accordingly, the prepared ester plasticizer may include terephthalate compounds substituted with a non-hybrid and non-branch type alkyl group, a hybrid and branch type alkyl group, and a non-hybrid and branch type alkyl group.

The expression "non-hybrid and non-branch type" used in the present invention denotes a structure including two kinds of linear hydrocarbons including the same substituted alkyl groups without a branched chain at symmetric sites of a phenyl group unless specifically mentioned otherwise.

Also, the expression "hybrid and branch type" used in the present invention denotes a structure including different substituted alkyl groups at symmetric sites of a phenyl group with one kind of branched chain unless specifically mentioned otherwise. For example, in the terephthalate compound substituted with the hybrid and branch type alkyl group, when one of two alkyl groups substituted at the symmetric sites of the phenyl group is a branch type alkyl group, the other alkyl group is a non-branch type alkyl group.

In the hybrid and branch type alkyl substituted terephthalate compound, the branch type alkyl group may be the same as the branch type alkyl group in the non-hybrid and branch type alkyl substituted terephthalate compound. The non-branch type alkyl group in the hybrid and branch type alkyl substituted terephthalate compound may be the same as the non-branch type alkyl group in the non-hybrid and non-branch type alkyl substituted terephthalate compound.

Furthermore, the expression "non-hybrid and branch type" used in the present invention denotes a structure including the same substituted alkyl groups at the symmetric site of a phenyl group with two kinds of branched chains unless specifically mentioned otherwise.

According to an embodiment of the present invention, the compound of Chemical Formula 1, for example, may include at least any one of dioctyl terephthalate, bis(2-propylheptyl) terephthalate, and di-(2-ethylhexyl)terephthalate (DEHTP). In this case, excellent processability and heat resistance may be obtained.

Also, the first alcohol of Chemical Formula 2 may include at least any one of butanol and 2-propyl heptanol.

According to an embodiment of the present invention, for example, di-(2-ethylhexyl)terephthalate (DEHTP) may be used as the compound of Chemical Formula 1, and butanol may be used as the first alcohol of Chemical Formula 2. In this case, it may be desirable in terms of improving the processability of a resin by having a short absorption rate with respect to the resin and a short fusion time.

In the case that di-(2-ethylhexyl)terephthalate (DEHTP) is used as the compound of Chemical Formula 1 and butanol is used as the first alcohol of Chemical Formula 2 according to the embodiment of the present invention, an ester plasticizer prepared by the transesterification reaction may include di-(2-ethylhexyl)terephthalate (DEHTP) of the following Chemical Formula 1-1, 1-butyl 4-(2-ethylhexyl)terephthalate (BEHTP) of the following Chemical Formula 5-1, and dibutyl terephthalate (DBTP) of the following Chemical Formula 6-1, and the composition of the ester plasticizer may be controlled according to the amount of the first alcohol of Chemical Formula 2 added.

[Chemical Formula 1-1]

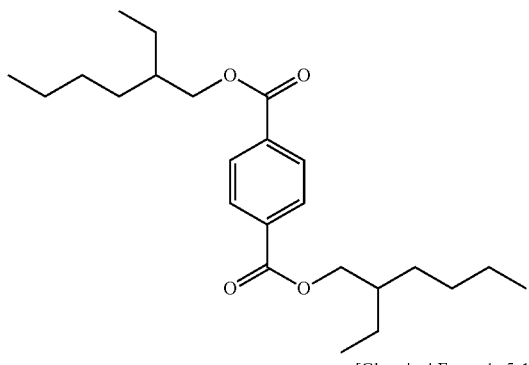

[Chemical Formula 5-1]

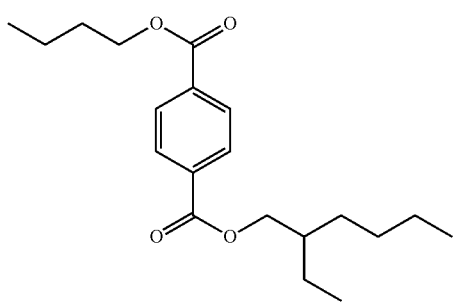

[Chemical Formula 6-1]

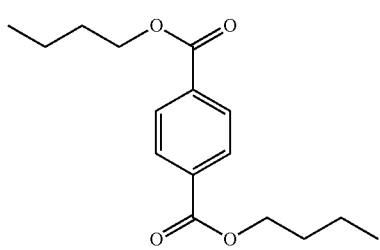

In the preparation method according to the embodiment of the present invention, when the transesterification reaction is conducted in the case that di-(2-ethylhexyl)terephthalate (DEHTP) is used as the compound of Chemical Formula 1 and butanol is used as the first alcohol of Chemical Formula 2 according to an embodiment of the present invention, the dibutyl terephthalate (DBTP) of the above Chemical Formula 6-1 may be formed when the butoxide ($C_4H_9O^-$) of the butanol of the above Chemical Formula 2 attacks the carbon atoms in two ester groups (ACOOR') substituted at the phenyl group in the di-(2-ethylhexyl)terephthalate (DEHTP) of the above Chemical Formula 1; the 1-butyl 4-(2-ethylhexyl) terephthalate (BEHTP) of the above Chemical Formula 5-1 may be formed when the butoxide ($C_4H_9O$—) of the butanol of the above Chemical Formula 2 attacks the carbon atom in one ester group (ACOOR') substituted at the phenyl group in the di-(2-ethylhexyl)terephthalate (DEHTP) of the above Chemical Formula 1; and the di-(2-ethylhexyl)terephthalate (DEHTP) of the above Chemical Formula 1 may remain as an unreacted portion in which the transesterification reaction is not performed.

According to an embodiment of the present invention, the ester plasticizer may include, in order of amount included, the di-(2-ethylhexyl)terephthalate (DEHTP) of the above Chemical Formula 1-1, the 1-butyl 4-(2-ethylhexyl)terephthalate (BEHTP) of the above Chemical Formula 5-1, and the dibutyl terephthalate (DBTP) of the above Chemical Formula 6-1 by the transesterification reaction. However, the mole fraction of the di-(2-ethylhexyl)terephthalate (DEHTP) participating in the transesterification reaction may be increased as the amount of the first alcohol of the above Chemical Formula 2 added increases. Thus, the amounts of the dibutyl terephthalate (DBTP) of the above Chemical Formula 6-1 and the 1-butyl 4-(2-ethylhexyl)terephthalate (BEHTP) of the above Chemical Formula 5-1 in the ester plasticizer may be increased.

Correspondingly, the amount of unreacted di-(2-ethylhexyl)terephthalate (DEHTP) of the above Chemical Formula 1-1 may tend to be decreased.

The present invention may provide an ester plasticizer that is prepared by the above preparation method.

An ester plasticizer according to an embodiment of the present invention may respectively include the compound of Chemical Formula 1, the compound of Chemical Formula 5, and the compound of Chemical Formula 6 in an amount of 25 wt % to 99 wt %, 0.5 wt % to 70 wt %, and 0.1 wt % to 20 wt %, and preferably, may respectively include the compound of Chemical Formula 1, the compound of Chemical Formula 5, and the compound of Chemical Formula 6 in an amount of 39 wt % to 85 wt %, 10 wt % to 60 wt %, and 0.5 wt % to 16 wt %.

According to an embodiment of the present invention, for example, in the case that di-(2-ethylhexyl)terephthalate (DEHTP) is used as the compound of Chemical Formula 1 and butanol is used as the first alcohol of Chemical Formula 2, an ester plasticizer prepared by the transesterification reaction may respectively include the dibutyl terephthalate (DBTP) of the above Chemical Formula 6-1, the 1-butyl 4-(2-ethylhexyl)terephthalate (BEHTP) of the above Chemical Formula 5-1, and the di-(2-ethylhexyl)terephthalate (DEHTP) of the above Chemical Formula 1-1 in an amount of 46.7 wt % to 85 wt %, 14.5 wt % to 43.8 wt %, and 0.5 wt % to 9.5 wt %, and most preferably, in an amount of 49.5 wt % to 83.2 wt %, 15.8 wt % to 42 wt %, and 1 wt % to 8.5 wt %.

Excellent processability and absorption rate of the resin may be obtained within the above range.

The ester plasticizer, for example, may be an ether-free plasticizer and may exhibit good plasticizing efficiency and good workability within the above range.

According to an embodiment of the present invention, the ether-free may denote that the amount of the ether component included in the plasticizer is 1,000 ppm or less, 100 ppm or less, or 10 ppm or less.

Also, the present invention may provide a resin composition including a plasticizer prepared by the above preparation method. The resin composition according to an embodiment of the present invention may be formed by including the ester plasticizer and a thermoplastic resin.

For example, the thermoplastic resin may be a vinyl-based resin or a vinyl chloride-based resin, and in this case, excellent workability and heat resistance may be obtained.

The vinyl-based resin is not particularly limited as long as it is recognized as a vinyl-based resin in the art, and the vinyl chloride-based resin is also not particularly limited as long as it is recognized as a vinyl chloride-based resin in the art.

The ester plasticizer, for example, may be included in an amount of 5 parts by weight to 100 parts by weight or 50 parts by weight to 90 parts by weight based on 100 parts by weight of the thermoplastic resin, and excellent workability and miscibility may be obtained within the above range.

For example, the resin composition may further include a filler.

The filler, for example, may be included in an amount of 10 parts by weight to 300 parts by weight, 50 parts by weight to 200 parts by weight, or 100 parts by weight to 200 parts by weight based on 100 parts by weight of the resin.

For example, the resin composition may further include at least one selected from the group consisting of a stabilizer, a pigment, a lubricant, and a foaming agent.

The stabilizer, pigment, lubricant, and foaming agent, for example, may each be included in an amount of 0.1 parts by weight to 20 parts by weight or 1 part by weight to 15 parts by weight based on 100 parts by weight of the resin.

Although, preferred examples are provided to allow for a clearer understanding of the present invention, they are mere examples of the present invention. It is obvious to those skilled in the art that various changes and modifications may be made therein without departing from the spirit and scope of the present invention, and such changes and modifications are intended to be covered by the appended claims.

EXAMPLES

Preparation Example 1

498.4 g of purified terephthalic acid (PIA), 1172.1 g of ethylhexyl alcohol (molar ratio of terephthalic acid:ethylhexyl alcohol=1:3), and 1.54 g (0.3 parts by weight based on 100 parts by weight of the terephthalic acid) of a titanium-based catalyst (tetra isopropyl titanate, TIPT) as a catalyst were put in a 3 liter, four-neck reactor equipped with a cooler, a water stripper, a condenser, a decanter, a reflux pump, a temperature controller, and a stirrer, and the temperature was slowly increased to about 170° C. The generation of water was initiated at about 170° C., and an esterification reaction was conducted for about 4.5 hours while continuously introducing nitrogen gas at a reaction temperature of about 220° C. under an atmospheric pressure condition. The reaction was terminated when an acid value reached 0.01.

After the completion of the reaction, distillation extraction was performed for 0.5 hours to 4 hours under reduced pressure in order to remove unreacted raw materials. Steam extraction was performed for 0.5 hours to 3 hours under reduced pressure using steam in order to remove the unreacted raw materials below a predetermined amount level. A temperature of a reaction solution was cooled to about 90° C. to perform a neutralization treatment using an alkaline solution. In addition, washing may also be performed and thereafter, water was removed by dehydrating the reaction solution. Filter media were introduced into the dehydrated reaction solution and stirred for a predetermined time. Then, the solution was filtered to finally obtain 1162 g (yield: 99.0%) of diethylhexyl terephthalate.

Preparation Example 2

Bis(2-propylheptyl)terephthalate was obtained in the same manner as in Preparation Example 1 except that 2-propylheptyl alcohol was used instead of ethylhexyl alcohol.

Example 1

1,000 g of di-(2-ethylhexyl)terephthalate (hereinafter, referred to as "DEHTP") and 70 g of butanol (7 parts by weight based on 100 parts by weight of the DEHTP) were introduced into a reactor equipped with a stirrer, a condenser, and a decanter, and transesterification reaction was conducted without a catalyst at a reaction temperature of 140° C. for 5 hours under a nitrogen atmosphere to obtain a reaction product including 98.9 wt % of DEHTP, 1.0 wt % of 1-butyl 4-(2-ethylhexyl)terephthalate (hereinafter, referred to as "BEHTP"), and 0.1 wt % of dibutyl terephthalate (hereinafter, referred to as "DBTP").

A mixture distillation of the reaction product was conducted to remove butyl alcohol and 2-ethylhexyl alcohol and to prepare a final ester plasticizer.

Changes in production amount (%) of BEHTP according to the transesterification reaction of Example 1 are illustrated in FIG. 1 below.

Example 2

Transesterification reaction was conducted in the same manner as in Example 1, except that the reaction temperature in Example 1 was changed to 160° C., to obtain a reaction product including 76.5 wt % of DEHTP, 21.5 wt % of BEHTP, and 2.0 wt % of DBTP. The product was distilled by the same method to prepare a final ester plasticizer.

Changes in production amount (%) of BEHTP according to the transesterification reaction of Example 2 are illustrated in FIG. 1 below.

Example 3

Transesterification reaction was conducted in the same manner as in Example 1, except that a titanium-based catalyst (tetra isopropyl titanate, TIPT) was added in an amount (1.0 g) corresponding to 0.1 wt % of the added amount of DEHTP, to obtain a reaction product including 95.0 wt % of DEHTP, 4.8 wt % of BEHTP, and 0.2 wt % of DBTP. The product was distilled by the same method to prepare a final ester plasticizer.

Changes in production amount (%) of BEHTP according to the transesterification reaction of Example 3 are illustrated in FIG. 1 below.

Example 4

Transesterification reaction was conducted in the same manner as in Example 2, except that a titanium-based catalyst (tetra isopropyl titanate, TIPT) was added in an amount (1.0 g) corresponding to 0.1 wt % of the added amount of DEHTP, to obtain a reaction product including 73.6 wt % of DEHTP, 24.0 wt % of BEHTP, and 2.4 wt % of DBTP. The product was distilled by the same method to prepare a final ester plasticizer.

Changes in production amount (%) of BEHTP according to the transesterification reaction of Example 4 are illustrated in FIG. 1 below.

Example 5

Transesterification reaction was conducted in the same manner as in Example 1, except that the reaction temperature in Example 1 was changed to 180° C. and a titanium-based catalyst (tetra isopropyl titanate, TIPT) was added in an amount (1.0 g) corresponding to 0.1 wt % of the added amount of DEHTP, to obtain a reaction product including 93.2 wt % of DEHTP, 6.3 wt % of BEHTP, and 0.5 wt % of DBTP. The product was distilled by the same method to prepare a final ester plasticizer.

Changes in production amount (%) of BEHTP according to the transesterification reaction of Example 5 are illustrated in FIG. 1 below.

Example 6

1,000 g of DEHTP and 130 g of BuOH (13 parts by weight based on 100 parts by weight of the DEHTP) were introduced into a reactor equipped with a stirrer, a condenser, and a decanter, and transesterification reaction was conducted by adding a titanium-based catalyst (tetra isopropyl titanate, TIPT) in an amount (10.0 g) corresponding to 1.0 wt % of the introduced amount of DEHTP at a reaction temperature of 160° C. for 5 hours under a nitrogen atmosphere to obtain a reaction product including 64.5 wt % of DEHTP, 32.0 wt % of BEHTP, and 3.5 wt % of DBTP.

A mixture distillation of the reaction product was conducted to remove butyl alcohol and 2-ethylhexyl alcohol and to prepare a final ester plasticizer.

Figure 2:
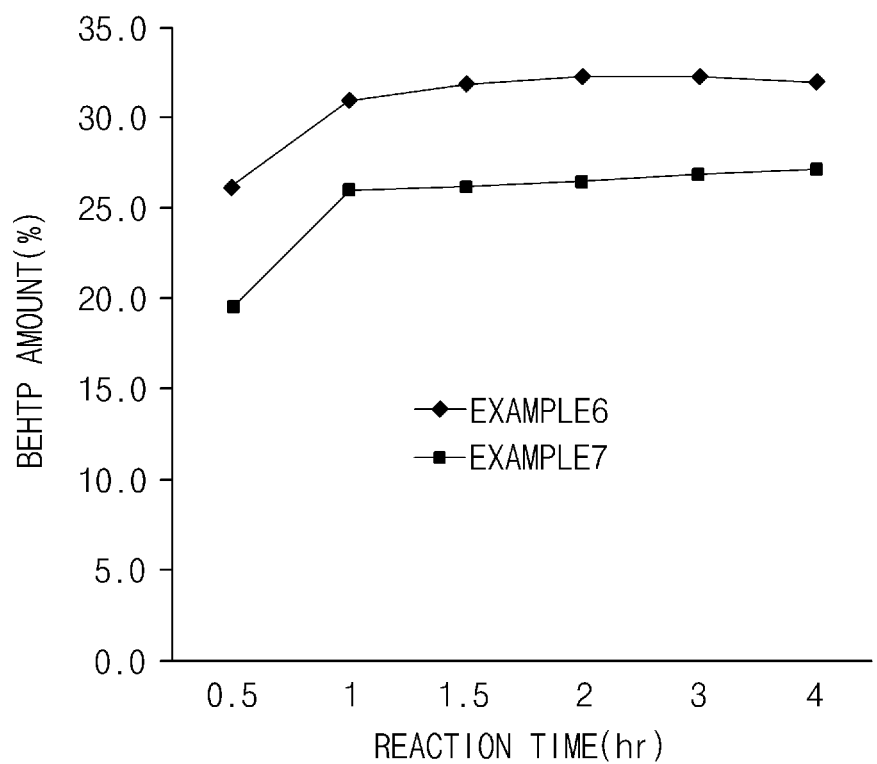
FIG. 2 is a graph illustrating changes in production amount of BEHTP according to an input amount of butanol of a transesterification reaction (reaction at 160° C.) according to an embodiment of the present invention.

Changes in production amount (%) of BEHTP according to the transesterification reaction of Example 6 are illustrated in FIG. 2 below.

Example 7

Transesterification reaction was conducted in the same manner as in Example 6, except that 100 g of BuOH (10 parts by weight based on 100 parts by weight of DEHTP) was used, to obtain a reaction product including 69.9 wt % of DEHTP, 27.1 wt % of BEHTP, and 3.0 wt % of DBTP. The product was distilled by the same method to prepare a final ester plasticizer.

Changes in production amount (%) of BEHTP according to the transesterification reaction of Example 7 are illustrated in FIG. 2 below.

Example 8

Transesterification reaction was conducted in the same manner as in Example 7, except that two-stage distillation, instead of mixture distillation, was used to respectively remove butanol and 2-ethylhexyl alcohol, to obtain a final ester plasticizer having a weight ratio of DEHTP:BEHTP:DBTP of 88.1:10.7:1.2.

Example 9

Transesterification reaction was conducted in the same manner as in Example 1, except that the reaction temperature in Example 1 was changed to 150° C., to obtain a reaction product including 86.5 wt % of DEHTP, 12.5 wt % of BEHTP, and 1.0 wt % of DBTP. The product was distilled by the same method to prepare a final ester plasticizer.

Changes in production amount (%) of BEHTP according to the reaction time of the transesterification reaction of Example 9 are illustrated in FIG. 1 below.

Example 10

Transesterification reaction was conducted in the same manner as in Example 1, except that the reaction temperature in Example 1 was changed to 170° C., to obtain a reaction product including 74.4 wt % of DEHTP, 23.1 wt % of BEHTP, and 2.5 wt % of DBTP. The product was distilled by the same method to prepare a final ester plasticizer.

Changes in production amount (%) of BEHTP according to the reaction time of the transesterification reaction of Example 10 are illustrated in FIG. 1 below.

Example 11

Transesterification reaction was conducted in the same manner as in Example 1, except that 70 g of 2-propyl heptanol (7 parts by weight based on 100 parts by weight of DEHTP) was used instead of 70 g of butanol, the reaction temperature in Example 1 was changed to 160° C., and a titanium-based catalyst (tetra isopropyl titanate, TIPT) was added in an amount (1.0 g) corresponding to 0.1 wt % of the added amount of DEHTP, to obtain a reaction product including 74 wt % of DEHTP, 24 wt % of 2-propylheptyl octyl terephthalate, and 2 wt % of bis(2-propylheptyl)terephthalate. The product was distilled by the same method to prepare a final ester plasticizer.

Example 12

Transesterification reaction was conducted in the same manner as in Example 1, except that bis(2-propylheptyl) terephthalate was used instead of di-(2-ethylhexyl)terephthalate, 70 g of 2-ethyl hexanol (7 parts by weight based on 100 parts by weight of DEHTP) was used instead of 70 g of butanol, the reaction temperature in Example 1 was changed to 160° C., and a titanium-based catalyst (tetra isopropyl titanate, TIPT) was added in an amount (1.0 g) corresponding to 0.1 wt % of the added amount of DEHTP, to obtain a reaction product including 73 wt % of bis(2-propylheptyl) terephthalate, 25 wt % of 2-propylheptyl ethylhexyl terephthalate, and 2 wt % of DEHTP. The product was distilled by the same method to prepare a final ester plasticizer.

Example 13

1,000 g of di-(2-ethylhexyl)terephthalate (hereinafter, referred to as "DEHTP") was introduced into a reactor equipped with a stirrer, a condenser and a decanter, and the temperature was increased to 160° C. Then, 40 g of butanol (4 parts by weight based on 100 parts by weight of the DEHTP) was transported with a pump and added into the reactor. Thereafter, transesterification reaction was conducted at a reaction temperature of 160° C. for 3 hours to obtain a reaction product including 0.5 wt % of dibutyl terephthalate (DBTP), 14.5 wt % of 1-butyl 4-(2-ethylhexyl)terephthalate (BEHTP) and 85 wt % of di-(2-ethylhexyl)terephthalate (DEHTP).

A mixture distillation of the reaction product was conducted to remove remaining butanol and 2-ethylhexyl alcohol and to prepare a final ester composition.

In the transesterification reaction in Example 1, changes in production amount (%) of DBTP according to an amount of the butanol added are illustrated in Table 3 below.

Example 14

An ester plasticizer having a composition listed in the following Table 3 was prepared in the same manner as in Example 13 except that 5 parts by weight of butanol was used based on 100 parts by weight of DEHTP.

Example 15

An ester plasticizer having a composition listed in the following Table 3 was prepared in the same manner as in Example 1 except that 8 parts by weight of butanol was used based on 100 parts by weight of DEHTP.

Example 16

An ester plasticizer having a composition listed in the following Table 3 was prepared in the same manner as in Example 13 except that 10 parts by weight of butanol was used based on 100 parts by weight of DEHTP.

Example 17

An ester plasticizer having a composition listed in the following Table 3 was prepared in the same manner as in Example 13 except that 15 parts by weight of butanol was used based on 100 parts by weight of DEHTP.

Example 18

An ester plasticizer having a composition listed in the following Table 3 was prepared in the same manner as in Example 13 except that 20 parts by weight of butanol was used based on 100 parts by weight of DEHTP.

Example 19

An ester plasticizer having a composition listed in the following Table 3 was prepared in the same manner as in Example 13 except that 23 parts by weight of butanol was used based on 100 parts by weight of DEHTP.

Comparative Example 1

Transesterification reaction was conducted in the same manner as in Example 1, except that 1,000 g of di-butyl terephthalate (DBTP) was used instead of DEHTP in Example 4 and 300 g of 2-ethylhexyl alcohol was added instead of BuOH to conduct the transesterification reaction for 5 hours, to obtain a reaction product including 4.3 wt % of BEHTP, 1.0 wt % of DEHTP, and 94.7 wt % of DBTP. The product was distilled by the same method to prepare a final ester plasticizer.

Comparative Example 2

Transesterification reaction was conducted in the same manner as in Example 1, except that the amount of the butanol in Example 4 was added in an amount (900 g) corresponding to 90 wt % of DEHTP, to obtain a reaction product including 17.2 wt % of DEHTP, 72.0 wt % of BEHTP, and 10.8 wt % of DBTP. The product was distilled by the same method to prepare a final ester plasticizer.

Comparative Example 3

498.4 g of purified terephthalic acid, 1015.8 g of ethylhexyl alcohol, 89 g of butyl alcohol, and 15 g (3 parts by weight based on 100 parts by weight of the PTA) of methanesulfonic acid (MSA) as a catalyst were put in a 3 liter, four-neck reactor equipped with a cooler, a water stripper, a condenser, a decanter, a reflux pump, a temperature controller, and a stirrer, and the temperature was slowly increased to about 210° C. The generation of water was initiated at about 170° C., and an esterification reaction was conducted for about 4 hours while continuously introducing nitrogen gas at a reaction temperature of about 210° C. under an atmospheric pressure condition. The reaction was terminated when an acid value reached 4.

After the completion of the reaction, distillation extraction was performed for 0.5 hours to 4 hours under reduced pressure in order to remove unreacted raw materials. Steam extraction was performed for 0.5 hours to 3 hours under reduced pressure using steam in order to remove the unreacted raw materials below a predetermined amount level. A temperature of a reaction solution was cooled to about 90° C. to perform a neutralization treatment using an alkaline solution. In addition, washing may also be performed and thereafter, water was removed by dehydrating the reaction solution. Filter media were introduced into the dehydrated reaction solution and stirred for a predetermined time. Then, the solution was filtered to finally obtain 1 wt % of dibutyl terephthalate (DBTP), 15 wt % of 1-butyl 4-(2-ethylhexyl) terephthalate (BEHTP), and 84 wt % of di-(2-ethylhexyl) terephthalate (DEHTP).

Comparative Example 4

2 wt % of DEHTP, 25 wt % of 2-propylheptyl ethylhexyl terephthalate, and 73 wt % of bis(2-propylheptyl)terephthalate were obtained in the same manner as in Comparative Example 3 except that 293 g of 2-ethyl hexanol and 1,067 g of 2-propyl heptanol were used as an alcohol.

Experimental Examples

Experimental Example 1

Physical properties of the plasticizers prepared in Examples 1 to 12 and Comparative Examples 1 and 2 were measured by the following methods, and the results thereof are presented in Table 1 and FIGS. 1 and 2 below.

amounts (wt %) of DEHTP, BEHTP, and DBTP: measured using a gas chromatograph system by Agilent Technologies (Agilent 7890 GC, column: HP-5, carrier gas: helium).

amount of ether: measured using a gas chromatograph system by Agilent Technologies (Agilent 7890 GC, column: HP-5, carrier gas: helium).

absorption rate: 400 g of PVC (LS 100) and 200 g of a plasticizer were mixed using a mixer (Brabender) under mixing conditions of 77° C. at 60 rpm. The time period from mixing the resin and the plasticizer to obtaining a stabilized state of the torque of the mixer (as a state, in which a peak of the torque was initially increased and then gradually decreased to be maintained almost horizontally, and the state was confirmed by a graph on a monitor) was measured and evaluated.

foamability: 100 parts by weight of PVC (PB 900), 75 parts by weight of a plasticizer, 130 parts by weight of a filler, 4 parts by weight of a stabilizer, 13 parts by weight of $TiO_2$, and 3 parts by weight of a foaming agent were mixed to prepare a sol. A base sheet (paper) used as wallpaper was thinly coated with the sol, and the sol is foamed at 230° C. for 70 seconds. Then, the sheet thus obtained was sectioned, and a cell state was observed with an optical microscope and evaluated on a 5-grade scale based on the degree of uniformity of size, shape, and arrangement of the cell (Grade 1 (good)~Grade 5 (poor)).

TABLE 1

|  | Catalyst (%) | Reaction temperature (° C.) | Reaction time (h) | Absorption rate (m:s) | Foama-bility |
|---|---|---|---|---|---|
| Example 1 | None | 140 | 5 | 6:10 | 3 |
| Example 2 | None | 160 | 5 | 4:30 | 1 |
| Example 3 | 0.1 | 140 | 5 | 6:00 | 4 |
| Example 4 | 0.1 | 160 | 5 | 4:11 | 1 |
| Example 5 | 0.1 | 180 | 5 | 5:48 | 3 |
| Example 6 | 1.0 | 160 | 4 | 3:42 | 1 |
| Example 7 | 1.0 | 160 | 4 | 4:01 | 1 |
| Example 8 | 1.0 | 160 | 4 | 5:58 | 2 |
| Example 9 | None | 150 | 5 | 5:50 | 3 |
| Example 10 | None | 170 | 5 | 4:25 | 1 |
| Example 11 | 0.1 | 160 | 5 | 6:28 | 4 |
| Example 12 | 0.1 | 160 | 5 | 7:02 | 4 |
| Comparative Example 1 | 0.1 | 160 | 5 | 2:13 | 4 |
| Comparative Example 2 | 0.1 | 160 | 5 | 2:52 | 3 |

* foamability: 1 (good)~5 (poor)

The method of preparing an ester plasticizer according to the embodiment of the present invention may freely prepare butyloctyl terephthalate according to the desired composition. Since all of the absorption rates of the ester plasticizers (Examples 1 to 12) prepared therefrom were excellent in a range of 3:42 to 7:02 (m:s) as illustrated in Table 1, it may be confirmed that workability was significantly improved and foamability of the resin was also significantly improved.

However, since the absorption rates of the ester plasticizers (Comparative Examples 1 and 2) prepared by a preparation method different from the method of preparing an ester plasticizer according to the embodiment of the present invention were excessively fast, gelation may be promoted. Thus, it may be confirmed that workability and foamability were significantly reduced.

Also, it may be confirmed that the method of preparing an ester plasticizer according to the embodiment of the present invention may not cause wastewater treatment problems because the reaction time was short and butanol, which was easily dissolved in water, was not generated as a by-product but only consumed.

As illustrated in FIG. 1 below (with respect to Examples 1 to 5 and Examples 9 and 10), in the transesterification reaction according to the present invention, since the production amount of BEHTP was greatly increased in a reaction temperature range of greater than about 140° C. to less than 180° C. for both cases in which a catalyst was used or was not used, it may be confirmed that an ester plasticizer having a desired composition was easily obtained.

As illustrated in FIG. 2 below (with respect to Examples 6 and 7), in the transesterification reaction according to the embodiment of the present invention, it may be confirmed that the production amount of BEHTP was constantly increased when the amount of butanol added was increased.

In a case where remaining alcohol was removed by a different distillation method after the transesterification reaction according to the embodiment of the present invention, it may be confirmed that the production amount of BEHTP by the two-stage distillation (Example 8) was significantly decreased in comparison to those by the mixture distillation (Examples 6 and 7).

In the ester plasticizers (Examples 1 to 12) according to the embodiment of the present invention, ether was detected in an amount of 100 ppm or less or was not detected using the gas chromatography (GC) analysis system.

Experimental Example 2

Measurement of Yield and By-Product According to Preparation Process

Yield, purity, and by-product of Examples 12 and 13 and Comparative Examples 3 and 4 were measured, and the results thereof are presented in Table 2 below.

TABLE 2

|  | Example 12 | Example 13 | Comparative Example 3 | Comparative Example 4 |
|---|---|---|---|---|
| Use acid catalyst | X | X | ○ | ○ |
| Yield | ↑99% | ↑99% | ↑98% | ↑98% |
| Purity | 99.8 | 99.9 | 98.9 | 98.7 |
| By-product | 0.2% | 0.1% | di-alkyl ethers 1.1% | di-alkyl ethers 1.3% |

As a result of measuring yield, purity, and by-product of Examples 12 and 13 subjected to the transesterification reaction and Comparative Examples 3 and 4 subjected to general esterification reaction as illustrated in Table 2, with respect to Examples 12 and 13, a yield of 99% or more was obtained despite of the fact that a catalyst was not used. In contrast, with respect to Comparative Examples 3 and 4, it may be understood that the yield thereof was decreased in an amount of 1% or more in comparison to Examples 12 and 13 of the present application.

Also, with respect to Examples 12 and 13, an amount of the by-product was about 0.2% or less. However, with respect to Comparative Examples 3 and 4, since an amount of the by-product was greater than 1%, it may be understood that the amount of the by-product was increased to 10 times or more that of Examples 12 and 13.

Experimental Example 3

Measurement of Amount of Ester Plasticizer

It may be understood that ester plasticizers of Examples 13 to 19 having various compositions may be obtained by adjusting the amount of butanol as illustrated in Table 3 below.

TABLE 3

|  | Amount of butanol added | DBTP | BEHTP | DEHTP |
|---|---|---|---|---|
| Example 13 | 4 parts by weight | 0.5 wt % | 14.5 wt % | 85.0 wt % |
| Example 14 | 5 parts by weight | 1.0 wt % | 15.8 wt % | 83.2 wt % |
| Example 15 | 8 parts by weight | 2.1 wt % | 24.2 wt % | 73.7 wt % |
| Example 16 | 10 parts by weight | 2.8 wt % | 28.4 wt % | 68.8 wt % |
| Example 17 | 15 parts by weight | 4.8 wt % | 35.1 wt % | 60.1 wt % |
| Example 18 | 20 parts by weight | 8.5 wt % | 42 wt % | 49.5 wt % |
| Example 19 | 23 parts by weight | 9.5 wt % | 43.8 wt % | 46.7 wt % |

In the ester plasticizers of Examples 13 to 19 of the present invention, the amounts (wt %) of the DBTP, the BEHTP and the DEHTP were measured using a gas chromatograph system by Agilent Technologies (Agilent 7890 GC, column: HP-5, carrier gas; helium).

Ether was not detected in the ester plasticizers of Examples 13 to 19.

From the result, composition ratios of the butanol, as a reactant, to the DBTP, the BEHTP, and the DEHTP, as products, and particularly, the relation of BEHTP/DBTP may be obtained. That is, in the ester plasticizers of Examples 13 to 19, it may be confirmed that a value of BEHTP/DBTP was in a range of 4.6 to 29. Also, as illustrated in Table 3, the amounts of the DBTP and BEHTP in the ester plasticizers were gradually increased as the amount of the butanol added was increased, and it may be confirmed that the amount of the DEHTP was correspondingly decreased.

Experimental Example 4

Sample (Sheet) Preparation and Performance Evaluation

The ester plasticizers prepared in Examples 13 to 19 were used. 55 parts by weight of the plasticizer, 2 parts by weight of a BZ stabilizer (BZ210, Songwon Industrial Co., Ltd.) as an additive, and 2 parts by weight of an epoxidized soybean oil (ESO, Songwon Industrial Co., Ltd.) were formulated based on 100 parts by weight of a polyvinyl chloride resin (PVC (LS 130s)) and then mixed at 1,300 rpm at 100° C. A sheet having a thickness of 2 mm was prepared by using a roll mill at 175° C. for 4 minutes and then using a press at 185° C. for 3 minutes (under a low pressure) and for 2 minutes and 30 seconds (under a high pressure).

Hardness, tensile strength, elongation rate, migration loss, sheet heating loss, heat stability, accelerated weathering (QUV), and absorption rate were evaluated for the sheet, and the fusion test was performed on the sheet.

Conditions of each performance evaluation are as follows.

Hardness Measurement

Shore hardness was measured at 25° C. in accordance with ASTM D2240.

Tensile Strength Measurement

A breaking point of a specimen was measured after pulling the specimen at a cross-head speed of 200 mm/min using a test instrument, U.T.M (4466, Instron) by the method of ASTM D638. The tensile strength was calculated as follows.

Tensile strength(kgf/mm$^2$)=load value(kgf)/(thickness (mm)×width(mm))

Elongation Rate Measurement

A breaking point of a specimen was measured after pulling the specimen at a cross-head speed of 200 mm/min using the U.T.M by the method of ASTM D638, and the elongation rate was calculated as follows.

Elongation rate(%)=length after elongation/initial length×100

Migration Loss Measurement

A specimen having a thickness of 2 mm or more was obtained in accordance with KSM-3156. ABS (natural color) was attached on both sides of the specimen, and the weight of 1 kgf/cm$^2$ was then applied thereto. The specimen was left standing for 72 hours in a hot air circulating oven (80° C.), and cooled at room temperature for 4 hours. Thereafter, the ABS attached to the both sides of the specimen was removed. Then, weights of the specimen before and after being left standing in the oven were measured, and the migration loss was calculated by the following equation.

Migration loss(%)={(initial weight of a specimen at room temperature−weight of the specimen after being left standing in an oven)/initial weight of the specimen at room temperature}×100

Sheet Heating Loss Measurement

The specimen thus prepared was heated at 70° C. for 72 hours, and the weight of the specimen was measured.

Loss on heating(wt %)={(initial weight of a specimen−weight of the specimen after heating at 70° C. for 72 hours)/initial weight of the specimen}×100

Heat Stability Measurement

The heat stability was measured by performing at a rate of 20 mm/30 seconds at 230° C.

QUV Measurement

In accordance with NIKE #G37 evaluation method, a sheet sample (10*10 cm sample) was evaluated after being left standing for 200 hours in a QUV apparatus by The Q-panel company under the following conditions.

QUV conditions: UV lamp: UVA-340/room temperature 22±2° C., and the measurement was conducted using a spectrometer (UV-3600).

Absorption Rate Measurement

PVC (LS 130s) and an ester plasticizer (plasticizer) were mixed by using a mixer (Brabender) under mixing conditions of 77° C. at 60 rpm. The time period from mixing the resin and the ester plasticizer (plasticizer) to obtaining a stabilized state of the torque of the mixer was measured and evaluated.

The stabilization of the torque denotes a state in which when the resin is first introduced and the ester plasticizer is then introduced to measure the absorption rate, a peak of the torque is initially increased and then gradually decreased to be maintained almost horizontally. The state may be confirmed by a graph on a monitor.

Fusion Test

The fusion test was conducted by processing a mixed sample under the conditions of 110° C./60 g/70 rpm.

The performance of each sample prepared by using Examples 13 to 19 was compared with those of samples respectively using dioctyl phthalate (DOP) alone, diisononyl phthalate (DINP) alone, and dibutyl terephthalate (DBTP) alone. The results of the performance tests measured by the above-described methods are illustrated in the following Table 4.

TABLE 4

| Performance evaluation | Example 13 | Example 14 | Example 15 | Example 16 | Example 17 | Example 18 | Example 19 | DOP | DNP | DBTP |
|---|---|---|---|---|---|---|---|---|---|---|
| Shore hardness (Shore "A") | 76.0 | 75.6 | 75.0 | 74.2 | 73.4 | 73.2 | 73.1 | 72.5 | 76.8 | 69.8 |
| Tensile strength (kg/mm$^2$) | 2.16 | 2.16 | 2.15 | 2.13 | 2.09 | 2.09 | 2.07 | 2.12 | 2.07 | 1.93 |
| Elongation rate (%) | 387 | 395 | 411 | 421 | 425 | 430 | 432 | 454 | 427 | 454 |

TABLE 4-continued

| Performance evaluation | Example 13 | Example 14 | Example 15 | Example 16 | Example 17 | Example 18 | Example 19 | DOP | DNP | DBTP |
|---|---|---|---|---|---|---|---|---|---|---|
| Migration loss (%) | 3.60 | 3.59 | 3.56 | 3.78 | 4.02 | 4.26 | 4.32 | 3.95 | 3.29 | 10.56 |
| Loss on heating (%) | 0.21 | 0.22 | 0.25 | 0.32 | 0.75 | 0.95 | 0.99 | 0.33 | 0.24 | 3.17 |
| Heat stability | Good | Good | Good | Good | Good | Good | Good | Ref | Good | Good |
| QUV | Light yellow | Same | Same | Same | Same | Same | Same | Ref | Same | Poor |
| Absorption rate (sec) | 6'34 | 6'27 | 6'15 | 5'45 | 5'03 | 4'32 | 4'15 | 5'06 | 6'20 | 1'40 |
| Fusion test (sec) | 102 | 75 | 50 | 48 | 42 | 39 | 36 | 32 | 45 | 22 |

As illustrated in Table 4, it may be confirmed that the sheets using Examples 13 to 19, in which 0.5 wt % to 9.5 wt % of DBTP was included in the ester plasticizers, exhibited better results in terms of all physical properties than the cases of using dioctyl phthalate (DOP) alone, diisononyl phthalate (DINP) alone, and dibutyl terephthalate (DBTP) alone.

In particular, since the absorption rate, fusibility, and hardness of Examples 13 to 19 were excellent, physical properties of the final product may be significantly different. Also, when the ester plasticizers of Examples 13 to 19 were used in an actual sheet, the amounts of the ester plasticizers may not only be decreased, but the good workability of the final product may also be stabilized.

Furthermore, in the heat stability and QUV test, the same results were obtained for Examples 14 to 19 as the case of using the DOP alone. The thermal stabilities of Examples 13 to 19 were better than the case of using the DOP alone.

With respect to Examples 13 to 19 of the present invention, it may be understood that the absorption rate of the resin was at least the same as or better than the cases of using the DOP or DINP. With respect to the DBTP, the absorption rate was somewhat short and this may act as poor physical properties when used in a product such as an actual sheet. The reason for this is that when the absorption rate is excessively short, a sufficient time for smooth processing the product may not be available, and thus, undesired product loss may occur.

Therefore, in a case where the amount of the DBTP was in a range of 0.5 wt % to 9.5 wt % as in the ester plasticizers of Examples 13 to 19, it may be confirmed that physical properties, such as hardness, tensile strength, elongation rate, migration loss, loss on heating, heat stability, QUV, absorption rate, and fusion test result, were generally better than the cases of using the DOP alone, the DINP alone, and the DBTP alone when the ester plasticizers were used in a sheet.

Experimental Example 4

Sample (Compound) Preparation and Performance Evaluation 50 parts by weight of the ester plasticizers prepared in Examples 13 to 19, 5 parts by weight of RUP 144 (Adeka Korea Co.), 40 parts by weight of Omya 1T (Omya), and 0.3 phr of St-A (Isu Chemical Co., Ltd.) were formulated based on 100 parts by weight of a polyvinyl chloride resin (PVC (LS100)) and then mixed at 1,300 rpm at 100° C. A sample having a thickness of 2 mm was prepared by using a roll mill at 175° C. for 4 minutes and then using a press at 185° C. for 3 minutes (under a low pressure) and for 2 minutes and 30 seconds (under a high pressure).

Hardness, tensile strength, elongation rate, migration loss, sheet heating loss, heat stability, accelerated weathering (QUV), and absorption rate were evaluated for the sample, and the fusion test was performed on the sample using a method similar to that of Experimental Example 3 under the experimental conditions listed in Table 5. The results of the performance evaluation for each sample are illustrated in the following Table 5.

In this case, stress test was conducted under the following conditions.

Stress test: A sample, in a state of being bent, was left standing for 7 days at room temperature, and degree of migration and deformation was observed.

TABLE 5

| Performance evaluation | | Example 13 | Example 14 | Example 15 | Example 16 | Example 17 | Example 18 | Example 19 | DOP | DNP | DBTP | Remarks |
|---|---|---|---|---|---|---|---|---|---|---|---|---|
| Shore hardness (Shore "A") | | 82.7 | 82.4 | 82.3 | 81.2 | 81.0 | 80.6 | 80.2 | 81.5 | 83.5 | 78 | Room temperature |
| Room temperature | Tensile strength (kg/mm$^2$) | 1.86 | 1.75 | 1.68 | 1.60 | 1.58 | 1.55 | 1.52 | 1.64 | 1.60 | 1.29 | 200 mm/min |
| | Elongation rate (%) | 291 | 290 | 288 | 280 | 275 | 274 | 270 | 286 | 287 | 232 | |
| After heating (100° C. × 168 hrs) | Tensile strength (kg/mm$^2$) | 1.66 | 1.63 | 1.66 | 1.65 | 1.58 | 1.62 | 1.60 | 1.65 | 1.54 | 1.35 | 100° C. × 168 hrs 200 mm/min |
| | Elongation rate (%) | 230 | 225 | 209 | 176 | 154 | 148 | 142 | 128 | 200 | 7 | |
| | Loss on heating (%) | 0.49 | 0.48 | 0.50 | 0.78 | 1.56 | 1.88 | 1.95 | 3.32 | 0.61 | 18.59 | 100° C. × 168 hrs |
| | QUV | same | same | same | same | same | same | same | ref | same | Light yellow | 200 hrs |

TABLE 5-continued

| Performance evaluation | Example 13 | Example 14 | Example 15 | Example 16 | Example 17 | Example 18 | Example 19 | DOP | DNP | DBTP | Remarks |
|---|---|---|---|---|---|---|---|---|---|---|---|
| Stress test | OK | OK | OK | OK | OK | OK | OK | OK | OK | OK | Room temperature, 7 days |
| Fusion test (sec) | 110 | 108 | 102 | 95 | 90 | 90 | 88 | 83 | 86 | 80 | 100° C./ 70 rpm |

As illustrated in Table 5, when Examples 13 to 19 were used in the compounds according to an embodiment of the present invention, it may be confirmed that equally desirable results in terms of all physical properties may be obtained in comparison to the cases of using the dioctyl phthalate (DOP) alone, the diisononyl phthalate (DINP) alone, and the dibutyl terephthalate (DBTP) alone.

In addition, with respect to the samples using the ester plasticizers of Examples 13 to 19, it may be understood that QUV, stress test results, and fusion test results as well as elongation rate and loss on heating were at least the same as or significantly better than the cases of using the DOP alone, the DINP alone, and the DBTP alone.

The results on the fusion test were designated from level 1 (fast fusion) to level 5 (slow fusion). With respect to Examples 13 to 19, the fusion test resulted in approximately level 2 and level 3. In contrast, the DBTP exhibited a short fusion time. The time required for smooth processing a product may be decreased due to the short fusion time, and product loss may occur. Thus, this may adversely affect processing.

In contrast, an excessively long fusion time as in the case of the DINP may reduce workability and productivity.

Thus, with respect to Examples 13 to 19 exhibiting an appropriate level of fusion time, good physical properties as well as process benefits may be provided when used in a product.

TABLE 6

| Performance evaluation | Example 13 | Example 14 | Example 15 | Example 16 | Example 17 | Example 18 | Example 19 | DOP | DNP | DBTP |
|---|---|---|---|---|---|---|---|---|---|---|
| Heat stability | Good | Good | Good | Good | Good | Good | Good | Ref | Same | Good |
| Fusion test | 3 | 2 | 2 | 2 | 2 | 2 | 2 | 3 | 5 | 1 |

Experimental Example 5

Sample (Plastisol) Preparation and Performance Evaluation 80 parts by weight of the ester plasticizers prepared in Examples 13 to 19, 90 parts by weight of Omya 10 (Omya) as a filler, 3 parts by weight of a K—Zn stabilizer (KKZ 102PF (Woochang Chemical Co., Ltd.)), 3 parts by weight of DWPX03 (Dongjin Co., Ltd.), 3 parts by weight of BYK4040 (BYK), 10 parts by weight of Dsol240R (Isu Chemical Co., Ltd.), and 12 parts by weight of $TiO_2$ were formulated based on 100 parts by weight of a polyvinyl chloride resin (PVC (PB900, LG Chem. Ltd.)).

Heat stability was evaluated for the plastisol, and fusion test was performed on the plastisol using a method similar to that of Experimental Example 3 under the experimental conditions listed in Table 6 below. In this case, the heat stability was evaluated under the following conditions.

Heat stability measurement: 30 mm/20 seconds at 230° C., pregelling at 150° C. for 45 seconds, coating to a thickness of 0.4 mm.

As illustrated in Table 6 below, when Examples 13 to 19 were used in the plastisols according to an embodiment of the present invention, it may be confirmed that excellent heat stability and fusion test results may be obtained in comparison to the cases of using the dioctyl phthalate (DOP) alone, the diisononyl phthalate (DINP) alone, and the dibutyl terephthalate (DBTP) alone.

In particular, with respect to Examples 13 to 19 of the present invention, it may be confirmed that excellent physical properties in terms of fusion may be obtained in comparison to the cases of using the DOP and DINP.

The invention claimed is:

1. A method of preparing an ester plasticizer, the method comprising conducting a transesterification reaction of a compound of Chemical Formula 1 with a first alcohol of Chemical Formula 2:

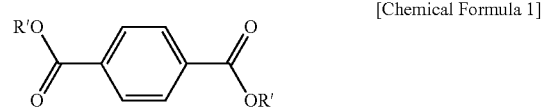

[Chemical Formula 1]

[Chemical Formula 2]

where R' is a non-branched $C_6$-$C_{12}$ alkyl or $C_6$-$C_{12}$ alkyl including at least one branched chain, R is a non-branched $C_4$-$C_{12}$ alkyl or $C_4$-$C_{12}$ alkyl including at least one branched chain, and R and R' are not the same as each other.

2. The method of claim 1, wherein the compound of Chemical Formula 1 is obtained by an esterification reaction between a compound of Chemical Formula 3 and a second alcohol of Chemical Formula 4 in the presence of a catalyst:

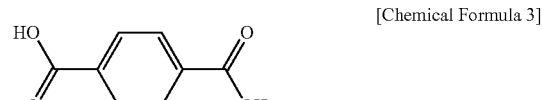

[Chemical Formula 3]

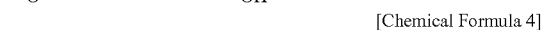

[Chemical Formula 4]

where R' is a non-branched $C_6$-$C_{12}$ alkyl or $C_6$-$C_{12}$ alkyl including at least one branched chain.

3. The method of claim 1, wherein a molar ratio of the compound of Chemical Formula 1 to the first alcohol of Chemical Formula 2 is in a range of 1:0.005 to 1:5.

4. The method of claim 1, wherein the first alcohol of Chemical Formula 2 is added in an amount of 0.1 parts by weight to 89.9 parts by weight based on 100 parts by weight of the compound of Chemical Formula 1.

5. The method of claim 4, wherein the first alcohol of Chemical Formula 2 is added in an amount of 3 parts by weight to 50 parts by weight based on 100 parts by weight of the compound of Chemical Formula 1.

6. The method of claim 2, wherein a boiling point of the first alcohol of Chemical Formula 2 is a lower temperature than an activation temperature of the catalyst.

7. The method of claim 1, wherein the transesterification reaction is conducted in a temperature range of 120° C. to 190° C.

8. The method of claim 1, wherein the transesterification reaction is a non-catalytic reaction.

9. The method of claim 2, wherein the esterification reaction is conducted in a temperature range of 80° C. to 270° C.

10. The method of claim 2, wherein the catalyst is an organic metal catalyst including a tin (Sn)-based or titanium (Ti)-based catalyst, an acid catalyst including a sulfonic acid-based or sulfuric acid-based catalyst, or a mixed catalyst thereof.

11. The method of claim 2, wherein the compound of Chemical Formula 3 and the second alcohol of Chemical Formula 4 are used in a molar ratio of 1:1 to 1:7.

12. The method of claim 1, further comprising removing unreacted first alcohol of Chemical Formula 2 after the transesterification reaction and a reaction by-product by distillation.

13. The method of claim 1, wherein a carbon number of R' of Chemical Formula 1 is greater than a carbon number of R of Chemical Formula 2.

14. The method of claim 1, wherein when R' of Chemical Formula 1 has at least one branched chain, R of Chemical Formula 2 is non-branched, and when R' of Chemical Formula 1 is non-branched, R of Chemical Formula 2 has at least one branched chain.

15. The method of claim 1, wherein the compound of Chemical Formula 1 comprises at least any one of dioctyl terephthalate, di-(2-ethylhexyl)terephthalate (DEHTP) and bis(2-propylheptyl)terephthalate.

16. The method of claim 1, wherein the first alcohol of Chemical Formula 2 comprises at least any one of butanol and 2-propyl heptanol.

17. The method of claim 13, wherein the compound of Chemical Formula 1 is di-(2-ethylhexyl)terephthalate (DEHTP), and the first alcohol of Chemical Formula 2 is butanol.

18. The method of claim 1, wherein a portion of the compound of Chemical Formula 1 is transformed into a compound of Chemical Formula 5 and a compound of Chemical Formula 6 by the transesterification reaction:

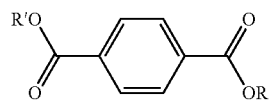

[Chemical Formula 5]

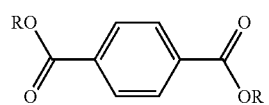

[Chemical Formula 6]

where R' is a non-branched $C_6$-$C_{12}$ alkyl or $C_6$-$C_{12}$ alkyl including at least one branched chain, R is a non-branched $C_4$-$C_{12}$ alkyl or $C_4$-$C_{12}$ alkyl including at least one branched chain, and R and R' are not the same as each other.

19. The method of claim 18, wherein the compound of Chemical Formula 1, the compound of Chemical Formula 5, and the compound of Chemical Formula 6 are respectively formed in an amount of 25 wt % to 99 wt %, 0.5 wt % to 70 wt %, and 0.1 wt % to 20 wt % based on a total weight of the ester plasticizer by the transesterification reaction.

20. The method of claim 19, wherein the compound of Chemical Formula 1, the compound of Chemical Formula 5, and the compound of Chemical Formula 6 are respectively formed in an amount of 39 wt % to 85 wt %, 10 wt % to 60 wt %, and 0.5 wt % to 16 wt % based on the total weight of the ester plasticizer by the transesterification reaction.

21. The method of claim 20, wherein the compound of Chemical Formula 1, the compound of Chemical Formula 5, and the compound of Chemical Formula 6 are respectively formed in an amount of 46.7 wt % to 85 wt %, 14.5 wt % to 43.8 wt %, and 0.5 wt % to 9.5 wt % based on the total weight of the ester plasticizer by the transesterification reaction.

22. The method of claim 21, wherein the compound of Chemical Formula 1 is di-(2-ethylhexyl)terephthalate, the compound of Chemical Formula 5 is 1-butyl 4-(2-ethylhexyl) terephthalate, and the compound of Chemical Formula 6 is dibutyl terephthalate.

* * * * *